United States Patent [19]
Evans et al.

[11] Patent Number: 5,702,914
[45] Date of Patent: Dec. 30, 1997

[54] USE OF REPORTER GENES FOR RETINOID RECEPTOR SCREENING ASSAYS HAVING NOVEL RETINOID-ASSOCIATED RESPONSE ELEMENTS

[75] Inventors: Ronald M. Evans, La Jolla; Toshihiko Ogura, San Diego, both of Calif.

[73] Assignee: The Salk Institute for Biological Studies, La Jolla, Calif.

[21] Appl. No.: 360,939

[22] Filed: Dec. 21, 1994

[51] Int. Cl.$^6$ .............................. C12N 15/67; C12Q 1/02
[52] U.S. Cl. ................... 435/29; 435/7.1; 435/7.6; 435/69.1; 536/24.1
[58] Field of Search ................... 435/7.1, 7.6, 29, 435/69.1; 536/24.1

[56] References Cited
PUBLICATIONS

Simeone, A., et al. (1990) *Nature* 346:763–766.
Langston, A. W., et al. (1994) *Curr. Opin. Genet. Dev.* 4: 550–55.
Scott, M. P. (1993) *Nucleic Acids Res.* 21: 1687–88.
Jonk, L. J., et al. (1994) *Dev. Biol.* 161: 604–14.
Bouillet, P., et al. (1995) *Dev. Biol.* 170: 420–33.
Ogura, T., et al. (1995) *Proc. Nat. Acad. Sci. USA* 92: 387–91.
Ogura, T., et al. (1995) *Proc. Nat. Acad. Sci. USA* 92: 392–96.

*Primary Examiner*—David L. Fitzgerald
*Attorney, Agent, or Firm*—Gray Cary Ware & Freidenrich; Stephen E. Reiter; Stanley H. Kim

[57] ABSTRACT

In accordance with the present invention, there are provided novel cotranscription factors that function to enhance mRNA transcription in cooperation with retinoid receptors. Also provided are novel DNA response elements, DNA constructs and expression vectors containing said constructs useful for providing cell-specific gene expression. Bioassays are also provided that are useful for evaluating whether a compound is a functional ligand (e.g., agonist or antagonist) for retinoid receptor protein(s), or functional engineered or modified forms thereof.

24 Claims, 9 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 167 base pairs
( B ) TYPE: nucleic acid ( C ) STRANDEDNESS: both
( D ) TOPOLOGY: both ( i i ) MOLECULE TYPE: DNA (genomic)

( x i ) SEQUENCE DESCRIPTION: SEQ ID NO:1:

| | | | | | |
|---|---|---|---|---|---|
| GAGCTCCGTT | GTTTATAGAG | ATCACTCCCT | GAACTCTTGC | CCTCCTGGAC | TTGCCCTAGC | 60 |
| TTCGGCCCCA | GGCTCCGGCC | AGGCAGACAC | CCTGACAGGT | TACAAATGAG | CGTGGGTGTT | 120 |
| GGATTGCCCC | AAGCTCTTGC | CCTCAAGTTG | TCCGGAGGAG | GAGAGTC | | 167 |

( 2 ) INFORMATION FOR SEQ ID NO:2:

( i ) SEQUENCE CHARACTERISTICS:
        ( A ) LENGTH: 146 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:2:

| | | | | | |
|---|---|---|---|---|---|
| GGCGGGCGGA | GGAGGCCGAG | GTAACCTGGG | ATCCGGGCC | TGACCTTTTT | ACCTCGAAGC | 60 |
| GCCTCTGGGC | TTTCCAAACA | AGCCGACAGC | GCGCCCGCGG | GGGCAGCTAT | TGTCTCCGGG | 120 |
| CCGGTCCCAC | TGGCAAACCT | TTGGTC | | | | 146 |

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:3:

CAGGCAGACA CCCTGACAGG TTACAAATGA GCGTGG     36

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:4:

AGGGCATCAG TTCA     14

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:5:

AGGTAATTAG GTCA     14

( 2 ) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: both
        (D) TOPOLOGY: both (ii) MOLECULE TYPE: other nucleic acid
        (A) DESCRIPTION: /desc = "Oligonucleotide"

(xi) SEQUENCE DESCRIPTION: SEQ ID NO:6:

AGCTACACCC TGACAGGTTA CAAATA                     26

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

RGBNNMNNRG BNNM                                  14

USE OF REPORTER GENES FOR RETINOID RECEPTOR SCREENING ASSAYS HAVING NOVEL RETINOID-ASSOCIATED RESPONSE ELEMENTS

ACKNOWLEDGEMENT

This invention was made with Government support under Grant Number 5 RO1 HD27183, awarded by the National institutes of Health. The Government has certain rights in this invention.

FIELD OF THE INVENTION

The present invention relates to retinoid associated transcription factor proteins, DNA response elements responsive thereto, and various uses therefor.

BACKGROUND OF THE INVENTION

Retinoids affect DNA transcription in a wide variety of mammalian cells. Retinoids exert their effects on transcriptional activity through intracellular retinoid receptors, which when complexed as heterodimers with a functional ligand bind to a specific retinoid response element, and subsequently modulate transcription. Previously, retinoic acid receptors (e.g., RAR and RXR) had been found to participate in modulation of nucleic acid transcription without requiring the binding of any co-factors, such as enhancers, and the like.

It has been found that RAR and RXR have a high degree of cooperativity in binding target DNA. For example, an RAR and RXR heterodimer binds to a DNA response element having two 6-nucleotide direct repeat sequences separated by a 5-nucleotide spacer sequence (DR-5), and strongly stimulates transcriptional activation (Kliewer et al., 1992, *Nature* 355:446–449). Indeed, RXR-TR and RXR-RAR heterodimers have been recently shown to bind related response elements (with different spacers), i.e., DR-4 and DR-5 sites, respectively (see, Perlman et al., 1993, *Genes Develop.* 7:1400–1422; and Kurokawa et al., 1993, *Genes Develop.*, 7:1423–1435). It has also been found that RXR-RAR heterodimers bind to a related DNA response element having two 6-nucleotide direct repeat sequences separated by a 2-nucleotide spacer sequence (DR-2) (Rhodes et al., 1993, *Genes Develop.* 7:913–932).

The mammalian homeobox genes (HOX) encode a family of more than 30 related proteins which share the common "homeo box" motif originally identified in a Drosophila homeotic complex. Human homeobox gene clusters designated HOX A, B, C, and D have been mapped to chromosomes 7, 17, 12, and 2, respectively, and retain a linear gene arrangement similar to their Drosophila counterparts (Acampora et al., 1989, NAR 17:10385–10402). Expression of mammalian homeobox genes is strictly regulated both temporally and spatially during embryonic development (see, e.g., Wilkinson et al., 1989, *Nature* 341:405–409).

Retinoic acid (RA), a natural metabolite of vitamin A has been proposed to be both a vertebrate morphogen and a regulator of the HOX gene clusters (see, e.g., Eichele, G., 1989, *Trends Genet.* 5:246–251). Systemic treatment of vertebrate embryos with retinoic acid results in severe developmental deformities, while local application of retinoic acid to chick limb bud produces digit duplication which is accompanied by a change of homeobox gene expression.

In the human embryonal carcinoma cell line NT2/D1 (Andrews et al., 1984, *Lab. Invest.* 50:147–162), homeobox genes are sequentially activated by retinoic acid in a graded fashion from the 3' to 5' direction. Activation of the 3' HOXB1 gene is not dependent on protein synthesis and thus is a candidate for direct regulation by retinoic acid. However, the precise molecular link between HOXB1 and retinoic acid signalling and the mechanism establishing graded chromosomal expression remains obscure. The actions of retinoic acid are mediated by both RARs and RXRs, members of retinoid nuclear receptor family (see, e.g., U.S. Pat. No. 5,171,671; Gigeure et al., 1987, *Nature* 330:624–629; Mangelsdorf et al., 1990, *Nature* 345:224–229; Mangelsdorf et al., 1992, *Genes and Develop.* 6:329–344, and the like). These receptors have been shown to function via a heterodimer, which binds DNA in a sequence specific manner. Binding of DNA serves to activate target genes through a retinoic acid responsive element (RARE) in a hormone dependent pathway.

Since the RARs and RXRs are essentially ubiquitous in their expression, the use of co-activators could provide a particularly effective means to restrict inducibility of a variety of genes by retinoic acid. Thus, retinoic acid induction could be limited to selective cell types in a cell-specific manner. For example, it has been found that a RARE in the promoter of the Pit-1 gene depends on Pit-1 for inducibility (Rhodes et al., 1993, *Genes Develop.* 7:913–932). How this occurs is unclear but may relate to the way in which heterodimers bind to target DNA.

Prior art bioassays employed for selecting functional ligands that bind retinoid receptors and modulate transactivation of protein expression employ retinoic acid receptor response elements (RAREs). Up to now these assays have only been able to identify ligands that modulate gene expression through the binding of a retinoic acid heterodimer to a response element having only the direct repeat sequence motif.

It would be desirable to improve upon prior art methods by developing bioassays that enable selection of cell-specific functional ligands (e.g., agonists or antagonists) for retinoid receptors. It would also be desirable to identify ligands for retinoid receptors that modulate gene expression in cooperation with other cell specific transcription factors.

BRIEF DESCRIPTION OF THE INVENTION

In accordance with the present invention, there are provided novel retinoid-related proteins. Invention retinoid-related proteins are useful, in cooperation with an activated retinoid receptor, to enhance transactivation of nucleic acid transcription from a suitable promoter-containing nucleic acid construct. In addition, invention retinoid-related proteins are useful in invention bioassays for identifying functional ligands for retinoid receptors.

In accordance with another embodiment of the present invention, there are provided enhanced DNA response elements comprising a retinoic acid responsive direct repeat sequence and a co-factor specific binding site. Invention response elements are useful, when combined with heterologous coding sequences, to promote cell specific transactivation of gene expression. Invention response elements are also useful to promote reporter gene expression in bioassays for identifying functional ligands for retinoid receptors.

In accordance with yet another embodiment of the invention there are provided DNA constructs, recombinant expression vectors, and host cells containing such constructs and vectors. Invention DNA constructs comprise invention response elements operatively linked to a promoter. Such constructs are useful to confer transcriptional activation activity on the promoter in the presence of a functional ligand and its associated retinoid receptor.

In accordance with still another embodiment of the present invention, there are provided bioassays useful for evaluating whether a compound is a functional ligand (e.g., agonist or antagonist) for retinoid receptor protein(s), or functional engineered or modified forms thereof.

BRIEF DESCRIPTION OF THE FIGURES

FIG. 1 provides results from assays for retinoic acid-dependent activation of HOXB1 promoter.

FIG. 2 provides results from an assay for retinoic acid-dependent transactivation by HOXB1 3' genomic region.

DETAILED DESCRIPTION OF THE INVENTION

Figure 1A:
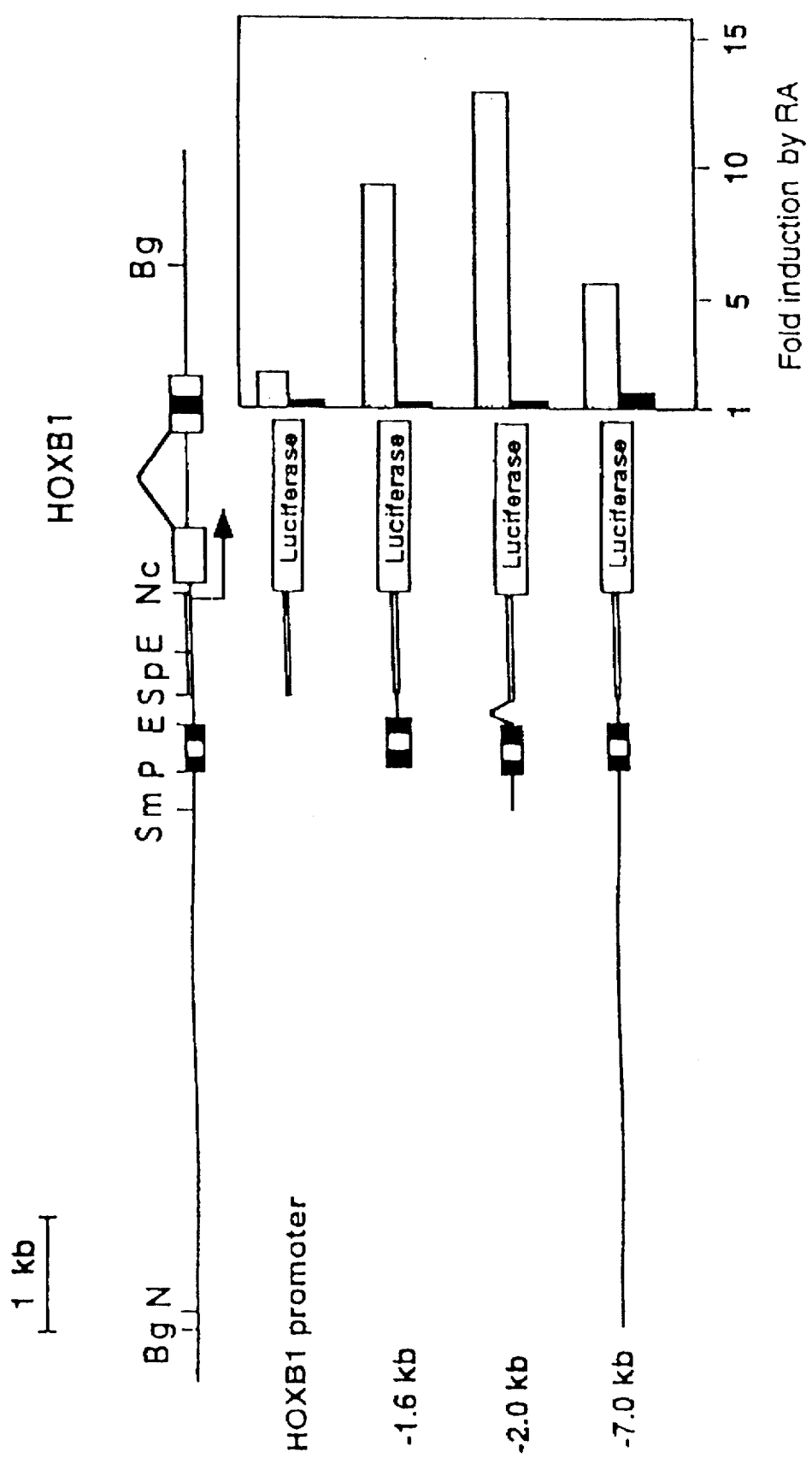
In FIG. 1(A), various 5' deletion constructs were transfected to P19 cells (shaded bars) and NT2/D1 cells (solid bars). The PstI-EcoRI region in the schematic contains a retinoic acid-responsive site. The transcription initiation site is indicated by an arrow. Fold induction by 1 µM of retinoic acid is plotted to the right of each construct. The 1 kb SpeI-NcoI fragment (double lined restriction map) was used as the basal HOXB1 promoter. Restriction site designations are as follows; Bg:BglII, E:EcoRI, Hf:HinfI, N:NdeI, Nc:NcoI, P:PstI, Sc:SacI, Sm:SmaI, Sp:SpeI.

In accordance with the present invention, there is provided an isolated retinoid-inducible-protein (RIP) characterized as binding to a RIP-binding-site having substantially the same nucleotide sequence as nucleotides 91–99 set forth in SEQ ID NO:1. The RIP, in cooperation with an activated retinoid receptor, enhances transactivation of nucleic acid transcription from a suitable nucleic acid construct. Such nucleic acid constructs comprise a promoter operatively associated with a retinoic acid-response element (RARE) and a RIP-binding-site.

Unexpectedly, it has been found that the association of RARE with a RIP-binding-site of the invention substantially enhances transcription activity cooperatively induced by an RAR-RXR heterodimer and RIP. It has also been found that expression of the endogenous RIP is induced by retinoic acid in P19 cells (Andrews et al., 1984, *Lab. Invest.* 50:147–162, incorporated herein by reference), but not in NT2/D1 cells (Andrews et al., 1984, supra).

As used herein, the phrase "isolated" as a modifier of invention proteins refers to proteins that have been manipulated, such that they are separated from their native in vivo cellular environment and are substantially free of other cellular proteins, respectively. Invention proteins are useful, for example, in the identification of selective drugs or compounds.

RIPs can be isolated so they are substantially free of other cellular proteins by, for example, using a nucleic acid having a RIP-binding-site sequence to bind the RIP protein, whereby the RIP-binding nucleic acid is bound to a solid support. Subsequently, the RIP-nucleic acid (protein-DNA) complex can be separated from other proteins, and RIP protein can then be eluted from the nucleic acid in substantially isolated form. RIPs have been isolated from P19 cells, which are derived from human embryonic carcinoma cells. Thus, cells derived from human embryos are a suitable source of RIPs.

As used herein, the phrase "binding" refers to the well-known interaction that occurs between DNA-binding proteins (e.g., transcription factors) and a particular DNA-binding site. The ability of a given protein to bind to a particular DNA-binding site can be assayed by numerous methods well-known in the art, such as in gel-shift assays described herein.

As used herein, the term "RIP-binding-site" (i.e., URE) refers to a nucleotide sequence that binds to a RIP at physiological conditions. Suitable RIP-binding-sites have substantially the same nucleotide sequence as nucleotides 91–99 in SEQ ID NO:1. A particularly preferred RIP-binding-site has the same nucleotide sequence as nucleotides 91–102 in SEQ ID NO:1. The invention RIP-binding-site, when operatively linked to a promoter having a RARE and a coding sequence, functions cooperatively with adjacent RAREs to confer full and cell-specific transcriptional activation of a desired coding region in response to retinoids.

As used herein, the phrase "substantially the same nucleotide sequence" refers to nucleic acids having sufficient homology to a reference polynucleotide, such that it will hybridize to the reference nucleotide under moderately stringent hybridization conditions. Alternatively, nucleic acids having "substantially the same nucleotide sequence" as the reference nucleotide sequence has at least 70% homology with respect to the reference nucleotide sequence. Nucleic acids having at least 80%, more preferably 90%, yet more preferably 95%, homology to the reference nucleotide sequence are also contemplated.

As used herein, the phrase "moderately stringent hybridization" refers to conditions that permit target-DNA to bind a complementary nucleic acid that has about 60%, preferably about 75%, more preferably about 85%, homology to the target DNA; with greater than about 90% homology to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

As used herein, the phrase "induced by retinoic acid" refers to the intracellular expression of RIP caused by exposure of the cell to retinoic acid, or derivatives thereof (e.g., retinoids). It has been found that RIP is induced by retinoic acid in P19 cells.

As used herein, the phrase "cooperative transactivation of transcription," or grammatical variations thereof, refers to a well-known mechanism of transcription where more than one transcription factor (e.g., co-factors) operate in tandem to activate transcription. For example, when RIP binds at a RIP-binding-site and an RAR-RXR heterodimer binds at an appropriate retinoic acid response element (RARE), these two binding events cooperatively and synergistically trans-activate transcription to a substantial level, relative to transcription levels for each binding event alone.

As used herein, the phrase "activated retinoid receptor" refers to the well-known retinoid receptor heterodimer complex that forms when bound by a functional ligand (e.g., retinoids, and the like), such that the dimeric receptor is able to bind to its appropriate response element and initiate mRNA transcription. Suitable retinoid receptors include, for example, RAR receptors (e.g., α, β, and γ; U.S. Pat. No. 5,171,671, incorporated herein by reference) and RXR receptors (e.g., α, β, and γ). In a particular embodiment, an activated retinoid receptor is an RAR-RXR heterodimer.

As employed herein, the term "retinoids" refers to naturally occurring compounds with vitamin A activity, synthetic analogs, and various metabolites thereof. The retinoids are a class of compounds consisting of four isoprenoid units joined in head-to-tail manner. Numerous retinoids have been identified, as described, for example, by Sporn, Roberts and Goodman in the two volume treatise entitled *The Retinoids* (Academic Press, N.Y., 1984), to which the reader is directed for further detail. Exemplary retinoids include retinol, retinyl acetate, retinyl hexadecanoate, α-retinyl, 4,14-retroretinol, deoxyretinol, anhydroretinol, 3,4-didehydroretinol, 15,15-dimethyl retinol, retinyl methyl ether, retinyl phosphate, mannosyl retinyl phosphate, retinol thioacetate, retinal (retinaldehyde), 3,4-didehydroretinal, retinylidene acetylacetone, retinylidene-1,3-cyclopentanedione, retinal oxime, retinaldehyde acetylhydrazone, retinoic acid, 4-hydroxyretinoic acid, 4-oxoretinoic acid, 5,6-dihydroretinoic acid, 5,6-epoxyretinoic acid, 5,8-epoxyretinoic acid, the open-chain $C_{20}$ analog of retinoic acid (i.e., (all-E-3,7,11,15-tetramethyl-2,4,6,8,10,12,14-hexadecaheptaenoic acid), 7,8-didehydroretinoic acid, 7,8-dihydroretinoic acid, "Acid" (E, E)-3-methyl-5-(2,6,6-trimethyl-2-cyclohexen-1-yl)-2,4-pentanedioic acid), "$C_{17}$ Acid" ((E,E,E)-5-methyl-7-(2,6,6-trimethyl-1-cyclohexen-1-yl)-2,4,6-hepatrienoic acid), "$C_{22}$ Acid" (14'-apo-γ, ψ-carotenoic acid), retinoic acid esters (e.g., methyl ester, ethyl ester, etc.), retinoic acid ethylamide, retinoic acid 2-hydroxyethylamide, methyl retinone, "$C_{18}$ Ketone" 6-methyl-8-(2,6,6-trimethyl-1-cyclohexen-1-yl)-3,5,7-ocatrien-2-one), and the like.

In accordance with another embodiment of the present invention, there is provided an isolated retinoid-activating-protein (RAP) characterized as binding to a RAP-binding-site having substantially the same nucleotide sequence as nucleotides 101–116 in SEQ ID NO:2. RAP is constitutively expressed in P19 and NT2/D1 cells (see, Andrews et al., 1984, *Lab. Invest.* 50:147–162), but not in CV-1 cells (ATCC #CCL 70). In addition RAP, in cooperation with an activated retinoid receptor, enhances transactivation of nucleic acid transcription from a suitable nucleic acid construct. Such nucleic acid constructs comprise a promoter operatively associated with a RARE and a RAP-binding-site. The association of RARE with a RAP-binding-site of the invention substantially enhances transcription activity cooperatively induced by an RAR-RXR heterodimer and RAP.

As used herein, the term "RAP-binding-site" (i.e., DRE) refers to a nucleotide sequence that binds RAP at physiological conditions. Invention RAP-binding-sites are useful in conjunction with RAREs to provide cell-specific transcription initiation. Suitable RAP-binding-sites have substantially the same nucleotide sequence as nucleotides 101–116 in SEQ ID NO:2. A particularly preferred RAP-binding-site has the same nucleotide sequence as nucleotides 86–116 in SEQ ID NO:2.

In accordance with yet another embodiment of the present invention, there is provided an isolated enhanced-response-element comprising:

(1) a RIP-binding-site having substantially the same nucleotide sequence as nucleotides 91–99 in SEQ ID NO:1, operatively linked to (2) a direct repeat sequence:

5'-RGBNNM-[(NN)-RGBNNM]$_y$-3', wherein each R is independently selected from A or G;
each B is independently selected from G, C, or T;
each N is independently selected from A, T, C, or G; and
each M is independently selected from A or C; with the proviso that at least 4 nucleotides of each -RGBNNM- group of nucleotides are identical with the nucleotides at comparable positions of the sequence -AGGTCA-, and y is at least 1 (up to about 10), preferably up to about 5.

An isolated "enhanced-response-element" having a RIP-binding-site (also referred to herein as a "RIP-associated response element"), refers to a nucleotide sequence motif that, when operatively linked to a promoter, confers transcriptional activation on the promoter in the presence of RIP and a functional ligand bound to its associated retinoid receptor (e.g., an RAR-RXR heterodimer). RIP-associated DNA response elements contain several functionally separable components, two of which are a RIP-binding-site and a "direct repeat" sequence also referred to herein as a "retinoic acid response element" (RARE).

The RIP-binding-site binds RIP, and the RARE binds an activated RAR-RXR heterodimer. It has been found through mobility shift analysis as well as co-transfection assays that the binding activity of RIP and the RAR-RXR heterodimer is cell-specific. In addition, RIP-associated response elements of the invention have been found to activate either the HOXB1 promoter or heterologous promoters (e.g., thymidine kinase promoter) from both the 5' or 3' direction. Thus, it is also contemplated to operatively link RIP-associated response elements with heterologous promoters so as to confer cell-specific retinoid-responsive recombinant expression of desired proteins.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Suitable half-sites having the -RGBNNM- motif for use in the invention "RIP-associated response element" include, for example, half-sites selected from -AGGGCA-, -AGTTCA-, -AGGTAA-, -AGGTCA-, -GGTTCA-, -GGGTTA-, -GGGTGA-, -AGGTGA-, or -GGGTCA-. A particularly preferred first -RGBNNM- group in the invention RIP-associated response element is -AGGGCA-. A particularly preferred second -RGBNNM- group in the invention RIP-associated response element is -AGTTCA-. The presently most preferred RARE for use in the invention "RIP-associated response element" is -AGGGCA-TC-AGTTCA- (SEQ ID NO:4).

In accordance with yet another embodiment of the present invention, there is provided an isolated enhanced-response-element comprising:

(1) a RAP-binding-site having substantially the same nucleotide sequence as nucleotides 101–116 in SEQ ID NO:2, operatively linked to (2) a direct repeat sequence, as described above.

An isolated "enhanced-response-element" having a RAP-binding-site (also referred to herein as a "RAP-associated response element"), refers to a nucleotide sequence motif that, when operatively linked to a promoter, confers transcriptional activation on the promoter in the presence of RAP and a functional ligand bound to its associated retinoid receptor (e.g., an RAR-RXR heterodimer). RAP-associated DNA response elements contain a RAP-binding-site and a "direct repeat" sequence also referred to herein as a "retinoic acid response element" (RARE).

A particularly preferred first -RGBNNM- group for use in the invention "RAP-associated response element" is -AGGTAA-. A particularly preferred second -RGBNNM- group in the invention RAP-associated response element is -AGGTCA-. The presently most preferred RARE for use in the invention "RAP-associated response element" is -AGGTAA-TT-AGGTCA- (SEQ ID NO:5).

In accordance with another embodiment of the invention, there is provided an isolated DNA construct comprising:

an enhanced-response-element operatively linked to a promoter, so as to confer transcriptional activation activity on said promoter in the presence of a functional ligand and its associated retinoid receptor, wherein said enhanced-response-element is selected from a RIP-associated response element or a RAP-associated response element, as described above.

As used herein, "DNA construct" refers to a segment of DNA that confers the ability to controllably induce nucleic acid transcription on a particular stretch of DNA. Invention DNA constructs are designed to be recombinantly interchangeable with numerous heterologous DNA fragments so that protein expression occurs when the construct is contacted with an activated retinoid receptor and either a RIP or RAP protein.

As used herein, the phrase "transcriptional activation activity" refers to the well-known ability of promoters to initiate the transcription of a coding strand into mRNA.

As used herein, the phrase "functional ligands" refers to any compound capable of binding to a retinoid receptor such that the pharmacological activity of the receptor is activated or inhibited. Compounds contemplated for screening as functional ligands in accordance with the invention bioassays include retinoid or retinoid-like ligands, as well as compounds which bear no particular structural or biological relatedness to retinoids. Suitable compounds may be obtained from well-known sources, e.g., from peptide libraries, chemical libraries, bacterial and yeast broths, plants, and the like.

Examples of compounds which bear no particular structural or biological relatedness to retinoids, but which are contemplated for screening in accordance with the bioassays of the present invention, include any compound that is an antagonist (i.e., is capable of blocking the action of retinoid receptors), or an agonist (i.e., is capable of promoting the action of retinoid receptors), such as, for example, alkaloids and other heterocyclic organic compounds, and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary heterologous promoters contemplated for use in the practice of the present invention include the SV40 early promoter, the cytomegalovirus (CMV) promoter, the mouse mammary tumor virus (MMTV) steroid-inducible promoter, the Herpes simplex virus thymidine kinase (TK) promoter, the Drosophila alcohol dehydrogenase promoter, Moloney murine leukemia virus (MMLV) promoter, and the like.

Invention DNA constructs, containing invention response elements, may optionally further comprise a gene which encodes a protein, such as a reporter protein. As used herein, the phrase "reporter protein" refers to a protein whose expression can be detected in a variety of well-known protein expression assays. Particularly preferred reporter proteins for use herein include, for example, proteins selected from luciferase, chloramphenicol acetyl transferase (CAT), β-galactosidase, or the like.

As used herein, an invention "recombinant expression vector" (or plasmid) refers to discrete elements that are used to introduce heterologous DNA into cells for either expression or replication thereof. Selection and use of such vehicles is well within the skill of the artisan.

An expression vector includes elements capable of expressing DNAs that are operatively linked with regulatory sequences (such as promoter regions) that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are those that are replicable in eukaryotic cells and/or prokaryotic cells, including those that remain episomal or those which integrate into the host cell genome.

Exemplary eukaryotic plasmid expression vectors include eukaryotic cassettes, such as the pSV-2 gpt system (Mulligan et al., 1979, Nature 277:108–114) and the expression cloning vector described by Genetics Institute (1985, Science 228:810–815). These plasmid vectors, when modified to contain an invention DNA construct, are able to provide at least some expression of the protein of interest in response to a retinoid, or the like.

Other plasmid base vectors which contain regulatory elements that can be operatively linked to the invention response elements are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the invention, there are also provided host cells transformed with invention expression vector(s). Invention expression vectors are introduced into suitable host cells to produce transformed cell lines that express a desired protein (such as a reporter protein). The resulting cell lines can then be produced in quantity for reproducible quantitative analysis of the effects of functional ligands on retinoid receptor function via invention RIP-associated and RAP-associated response elements. The transfected mammalian cells may also be used in the methods of drug screening provided herein.

Suitable host cells in which DNA or RNA may be introduced include both eukaryotic and prokaryotic cells. Preferred eukaryotic cells are those that can be transiently or stably transfected and also express the DNA and RNA. Such cells may be identified empirically or selected from among those known to be readily transfected or transduced. Suitable prokaryotic cells are well-known in the art, and are those that are useful for preparing large quantities (clones) of invention expression vectors.

Exemplary eukaryotic cells for introducing invention expression vectors include, e.g., P19 cells and NT2/D1 cells (which are derived from human embryo carcinomas), COS cells, mouse L cells, Chinese hamster ovary (CHO) cells, human embryonic kidney cells, African green monkey cells, HEK 293 (ATCC accession #CRL 1573; U.S. Pat. No. 5,024,939), Ltk⁻ cells (ATCC accession #CCL1.3), COS-7 cells (ATCC under accession #CRL 1651), and DG44 cells (dhfr⁻ CHO cells; see, e.g., Urlaub et al. (1986) Cell. Molec. Genet. 12: 555). Presently preferred cells include P19 cells and NT2/D1 cells.

For invention bioassays in which a RIP-associated response element is employed to activate transcription of the reporter gene, P19 cells are preferred. For invention bioassays in which a RAP-associated response element is employed to activate transcription of the reporter gene, both P19 cells and NT2/D1 cells are preferred.

Suitable means for introducing (transforming) vectors into host cells to produce transduced recombinant cells (i.e., a cell containing a recombinant heterologous nucleic acid) are well-known in the art (see, for review, Friedmann, 1989, Science 244:1275–1281; Mulligan, 1993, Science 260:926–932, each of which are incorporated herein by reference in their entirety). Exemplary methods of transduction include, e.g., infection employing viral vectors (see, e.g., U.S. Patent 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like.

In accordance with a still further embodiment of the invention, there is provided a bioassay for evaluating whether a compound is a functional ligand for retinoid receptor protein(s), or functional engineered or modified forms thereof, said bioassay comprising:

(a) culturing cells which contain:

retinoid receptor protein(s), or functional engineered or modified forms thereof, a protein selected from RIP or RAP, DNA which encodes an enhanced-response-element operatively linked to a reporter gene, wherein said enhanced-response-element is selected from a RIP-associated response element or a RAP-associated response element, wherein said culturing is conducted in the presence of at least one compound whose ability to function as a ligand for said retinoid receptor protein, or functional engineered or modified forms thereof, is sought to be determined; and (b) assaying for evidence of transcription of said reporter gene in said cells.

As used herein, the phrase "functional engineered or modified forms" of retinoid receptors refers to non-naturally occurring receptors, such as recombinant retinoid receptors, produced by well-known methods. For example, the production of functional recombinant steroid/thyroid nuclear receptors by interchanging functional ligand-binding and DNA-binding domains is well-known to those of skill in the art (e.g., Evans et al., 1988, Science 240:889–895; U.S. Pat. No. 5,171,671, and the like). Thus, any recombinant nuclear receptor containing a functional domain, preferably a DNA-binding domain, derived from a retinoid receptor is contemplated for use herein.

As used herein, the phrase "heterologous DNA" refers to a genetically engineered DNA not already possessed by the recipient (e.g., exogenous or non-endogenous). The heterologous DNA is introduced into the cells as part of an invention expression vector by any of a variety of well-known methods, such as calcium-phosphate transfection, viral-vector infection, and the like.

As used herein, the phrase "RAR-RXR heterodimer complex" refers to a protein complex between any one of the RAR receptors (e.g., α, β, and γ; see U.S. Pat. No. 5,171,671) and any one of the RXR receptors (e.g., α, β, and γ). The heterodimer, when functioning to transactivate gene expression in cooperation with either RIP or RAP, binds to RAREs of the DR-2 class (i.e., a 6 nucleotide direct repeat sequence having a spacer of 2 nucleotides between repeats), such as those provided in SEQ ID NO:1 (nucleotides 30–43) and SEQ ID NO:2 (nucleotides 41–54).

As used herein, the phrase "assaying for evidence of transcription" refers to well-known methods for detecting the various products of transcription, such as mRNA or the corresponding amino acid sequence. Exemplary methods for detecting evidence of transcription include, for example, the cis/trans assay described in U.S. Pat. Nos. 5,171,671 and 4,981,784, (each of which are incorporated herein by reference), and the like.

In yet another embodiment of the invention, there is provided a bioassay for detecting compounds that are antagonists for retinoid receptor(s) or functional modified forms thereof, said bioassay comprising:

(a) culturing test cells in culture medium containing:

increasing concentrations of at least one compound whose ability to inhibit the transcription activation activity of retinoid receptor agonists is sought to be determined, and a fixed concentration of at least one agonist for said retinoid receptor(s) or functional modified forms thereof, wherein said test cells contain:

retinoid receptor(s) or functional modified forms thereof, a protein selected from RIP or RAP, DNA which encodes an enhanced-response-element operatively linked to a reporter gene, wherein said enhanced-response-element is selected from a RIP-associated response element and a RAP-associated response element, and thereafter (b) determining the amount of transcription of said reporter gene in said cells as a function of the concentration of said compound in said culture medium, thereby indicating the ability of said compound to inhibit activation of transcription by retinoid receptor agonists.

The invention assay is particularly useful for identifying compounds that inhibit ligand-binding to retinoid receptors, or inhibit activated retinoid receptor-binding to DNA response elements, or inhibit activated receptor-binding to cofactors required for transcription (e.g., RIP or RAP).

The phrase "agonists of retinoid receptors" refers to compounds that are able to form a complex with retinoid receptors and bind a respective DNA response element, so that the receptor-ligand complex is able to participate in transactivation or transrepression of nucleic acid transcription.

The phrase "antagonists of retinoid receptors" refers to compounds that are able to inhibit agonist activity, such that functional receptor binding to a particular DNA response element is inhibited. Antagonists can act mechanistically by either inhibiting ligand-binding to a respective receptor, or by inhibiting an activated ligand-receptor complex from binding to its respective DNA response element, or by inhibiting an activated ligand-receptor complex from binding to a cofactor required for the activation of transcription.

As used herein, the phrase "inhibit activation of transcription" refers to blocking the well known process whereby mRNA is transcribed from a respective cDNA coding sequence. The amount of mRNA transcription can be detected by a variety of methods well-known in the art, such as detecting levels of reporter protein expression, detecting directly the level of mRNA transcribed, and the like.

In accordance with yet a further embodiment of the invention, there is provided a method for testing the activity of a test compound as an agonist for a retinoid receptor, said method comprising:

(a) culturing host cells containing an invention expression vector in the presence of an intracellular retinoid receptor, an intracellular protein selected from RIP or RAP, and in the further presence, or in the absence, of the test compound; and thereafter (b) selecting test compounds that increase the amount of reporter protein expression relative to expression levels in the absence of said test compound.

Intracellular retinoid receptors and RIP or RAP proteins can be obtained by selecting a host cell that endogenously expresses either of these proteins. Retinoid receptors, RIP and RAP proteins can also be introduced into cells employing well-known recombinant DNA methods by introducing expression plasmids encoding these proteins into the test cells.

As used herein, the phrase "compounds that increase the amount of reporter protein expression relative to expression levels in the absence of said test compound" refers to compounds whose presence causes a higher level of reporter protein expression driven by an invention RIP-associated or RAP-associated expression construct, relative to protein expression in the absence of the test compound.

In accordance with yet a further embodiment of the invention, there is provided a method for testing the activity of a test compound as an antagonist of ligand for a retinoid receptor, said method comprising:

(a) culturing host cells containing an invention expression vector in the presence of an intracellular retinoid receptor, an intracellular protein selected from RIP or RAP, said ligand, and further:

(i) in the presence of the test compound, or (ii) in the absence of the test compound; and thereafter (b) selecting test compounds that decrease the amount of reporter protein expression relative to expression levels in the absence of said test compound.

The nomenclature used hereafter and the laboratory procedures in recombinant DNA technology described below are those well known and commonly employed in the art. Standard techniques are used for cloning, DNA and RNA isolation, amplification and purification. Enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., (1989). Other general references are provided throughout this document. The procedures therein are well known in the art and are described herein for the convenience of the reader. All the information contained therein is incorporated herein by reference.

The invention will now be described in greater detail by reference to the following non-limiting examples.

METHODS

DNA fragments containing the TK-Luciferase gene were ligated into the SalI site of the vector pBluescript SK+ (Stratagene) using Sal1 linkers to produce the plasmid pBS.TK.Luc. The TK promoter of pBS.TK.Luc was replaced by various genomic DNA fragments derived from the 5' region of the human HOXB1 gene (Acampora et al., 1989, NAR, 17(24):10385–10402). The SpeI-NcoI fragment of the 5' region was used as a basal HOXB1 promoter. Oligonucleotides used for plasmid construction and gel retardation assay were as follows: DR-2A (corresponding to nucleotides 23–51 of SEQ ID NO:1); LYRE (corresponding to nucleotides 80–115 of SEQ ID NO:1), and LYRE mutant (5'-CAGGCAGACACACTAGTAGGTTACAAATGAGC GTGG-3'; SEQ ID NO:3).

Cell Cultures and Transfections

Embryonal carcinoma cell line P19 and NT2/D1 (Andrews et al., 1984, Lab. Invest. 50:147–162) were grown in Dulbecco's modified Eagle's medium (DMEM) supplemented with 10% fetal bovine serum (Irvine Scientific). Twenty-four hours (1 hour for P19 cells) before transfection, cells were split in fresh medium described above. Transfections were performed via the calcium-phosphate precipitation method as described in Kliewer et al., (1992) *Nature* 355:446–449. 5 µg of the respective reporter luciferase plasmid and 7 µg of pCMX-βGAL (as internal control) were transfected into appropriate cells. After 12 hours, DNA precipitates were washed and cells were cultured with fresh medium containing 1 µM of retinoic acid for another 24 hours. Cells were harvested and the luciferase assay was carried out according to methods described in De Wet et al., (1987) *Mol. Cell. Biol.* 7:725–737. Transfection efficiency was normalized using β-galactosidase activity derived from pCMX-βGAL.

Gel Retardation Assays

Gel retardation assays were carried out according to Kliewer et al. (1992, supra). The plasmids pCMX-hRARα and pCMX-hRXRα (Kliewer et al., 1992, supra) were linearlized and capped mRNA was synthesized in vitro using T7 RNA polymerase (Stratagene) according to manufacturer's instructions. Aliquots of mRNA were incubated with rabbit reticulocyte lysate (Promega) for in vitro translation. For gel retardation assay, 5 µl of in vitro translated proteins were preincubated in binding buffer (10 mM Tris[pH8.0], 40 mM KCl, 0.05% Nonidet P-40, 6% glycerol, 1 mM DTT, 5 µg/ml poly[dI.dC]) on ice for 15 minutes. For competition assays, 20 fold molar excess of competitor oligonucleotides was mixed at this step. Oligonucleotides containing DR-5 (RARβ2RARE), HOXB DR-2A (nucleotides 30–43 of SEQ ID NO:1) and HOXB DR-2B (nucleotides 41–54 of SEQ ID NO:2) were used as competitors and probes. Subsequently, $^{32}$P-labelled oligonucleotide probes were added to the reaction mixtures and incubated on ice for 15 minutes. The same oligonucleotides used for the construction of luciferase plasmids were used. Reaction mixtures were resolved by 5% polyacrylamide gel electrophoresis in 0.5×TBE. The dried gels were autoradiographed at −70° C.

Nuclear extracts from P19 and NT2/D1 cells were prepared according to Digman et al., (1983) *NAR* 11:1475–1489, and cultured for 2 days in the presence or absence of 1 µM of retinoic acid, and subsequently stored at −80° C. Approximately 3–5 µg of protein was used for each reaction. A 20-fold excess of unlabelled oligonucleotides were used for competition experiments.

EXAMPLE 1

Figure 1B:
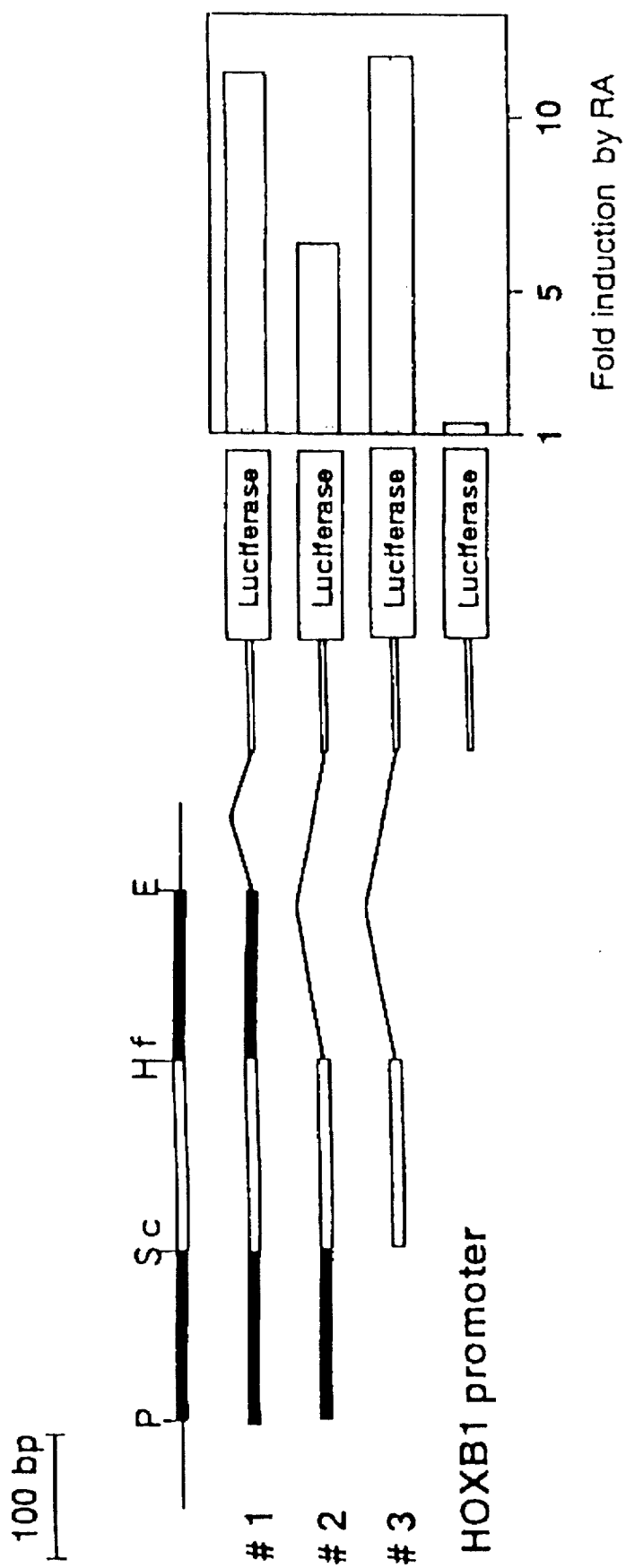
FIG. 1(B) provides a more detailed transfection analysis of the PstI-EcoRI fragment. It is seen that the retinoic acid-responsive site is localized to a 160 bp SacI-HinfIm region (indicated by open box).

Isolation of Retinoic Acid Responsive Site in the Promoter Region of the HOXB1 Gene To analyze the regulatory elements of HOXB1, an overlapping set of large chromosomal fragments was isolated and ligated to a luciferase reporter gene. As shown in FIG. 1a, a 7 kb fragment spanning the HOXB1 promoter was transfected into two embryonal carcinoma cell lines; P19 cells (shaded bars) and NT2/D1 cells (solid bars). In P19 cells but not in NT2/D1 cells, this plasmid was strongly induced by 1 µM of retinoic acid. Reporter constructs containing either −2.0 kb or −1.6 kb of upstream sequence retained full retinoic acid responsiveness, whereas deletions containing only −1.2 kb of upstream sequence or less produced only marginal induction. This data indicates the presence of a specific enhancer (i.e., RIP-associated response element) in an approximately 400 bp region between PstI and EcoRI restriction endonuclease sites (FIG. 1b).

Figure 1C:
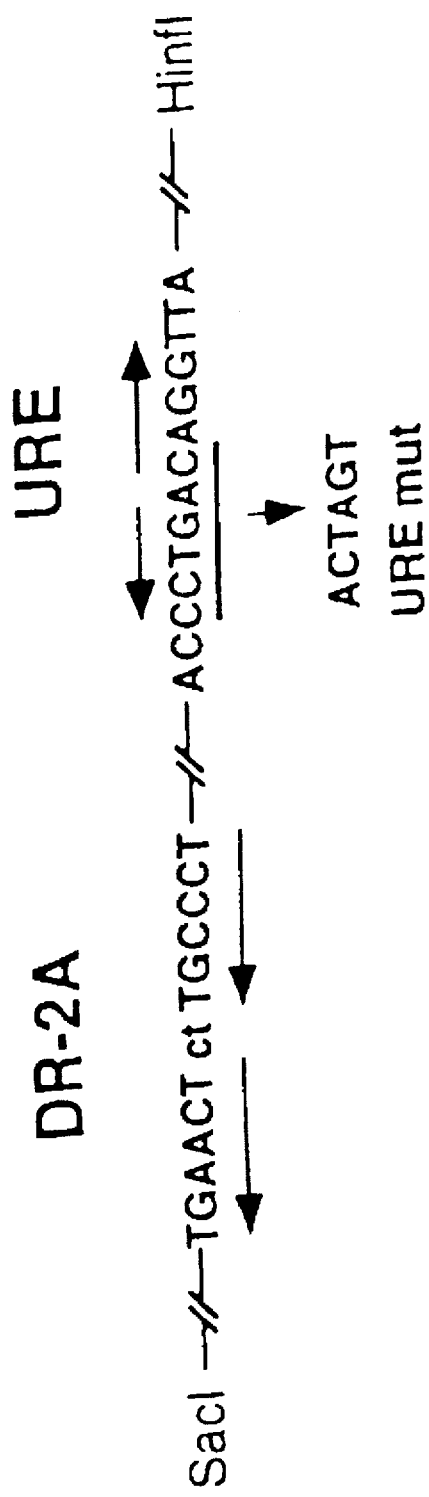
FIG. 1(C) presents the nucleotide sequence of DR-2A and the URE region. The palindromic sequence of the URE (Upstream Responsive Element) is indicated by opposing arrows. A mutation (URE mut) was introduced as indicated and used for both the construction of expression plasmids and the gel retardation assay. The binding site of RAR-RXR heterodimer is indicated by head-to-tail arrows (DR-2A).

This 400 bp region was examined in more detail. Retinoic acid activation was localized to a 160 nucleotide SacI-HinfI subfragment (FIG. 1b). A single copy of this 160 nucleotide region in front of the HOXB1 promoter confers a 13-fold induction to retinoic acid. The nucleotide sequence of the enhancer region is shown in FIG. 1c (SEQ ID NO:1). Inspection of the sequence reveals the presence of a palindrome referred to as the upstream response element (also referred to herein as the RIP-binding-site; nucleotides 91–99 of SEQ ID NO:1), as well as a direct repeat of the sequence AGGTCA, which forms the core binding site for the retinoic acid and retinoid X receptor and is observed in the antisense position at nucleotides 30–43 of SEQ ID NO:1 (designated DR-2A). While the RIP-binding-site contains no homology to known retinoic acid response elements, it has been found to substantially enhance the retinoic acid response of the HOX reporter. The 160 bp SacI-HinfI fragment confers robust retinoic acid induction on HOXB1 promoter, whereas activation is severely repressed (to 25%) following mutation of the RIP-binding-site (URE), as shown in FIG. 1c.

Other RIP-binding-site mutants were tested for the ability to bind RIP. The results are shown in Table 1.

TABLE 1

|  |  | RIP Binding |
|---|---|---|
| URE-wt | AG CTA CAC CCT GAC AGG TTA CAA ATA | +++ |
| mut 1 | ———— TCA ———————————————— | +++ |
| mut 2 | ———————— AAG ———————————— | + |
| mut 3 | ———————————— AGT ———————— | − |
| mut 4 | ———————————————— GAT ———— | + |
| mut 5 | ———————————————————— CCG — | + |

URE-wt corresponds to SEQ ID NO:6. The results indicate that either the first or third triplet of the 9 base pair RIP-binding site palindrome (nucleotides 9–17 of SEQ ID NO:6) can be modified while still retaining RIP binding function. Modification of the middle triplet corresponding to nucleotides 94–96 of SEQ ID NO:1 abolishes binding to RIP. In addition, modification of the 3 nucleotides immediately downstream of the palindrome (nucleotides 100–102 of SEQ ID NO:1) reduces the level of RIP binding.

Figure 1D:
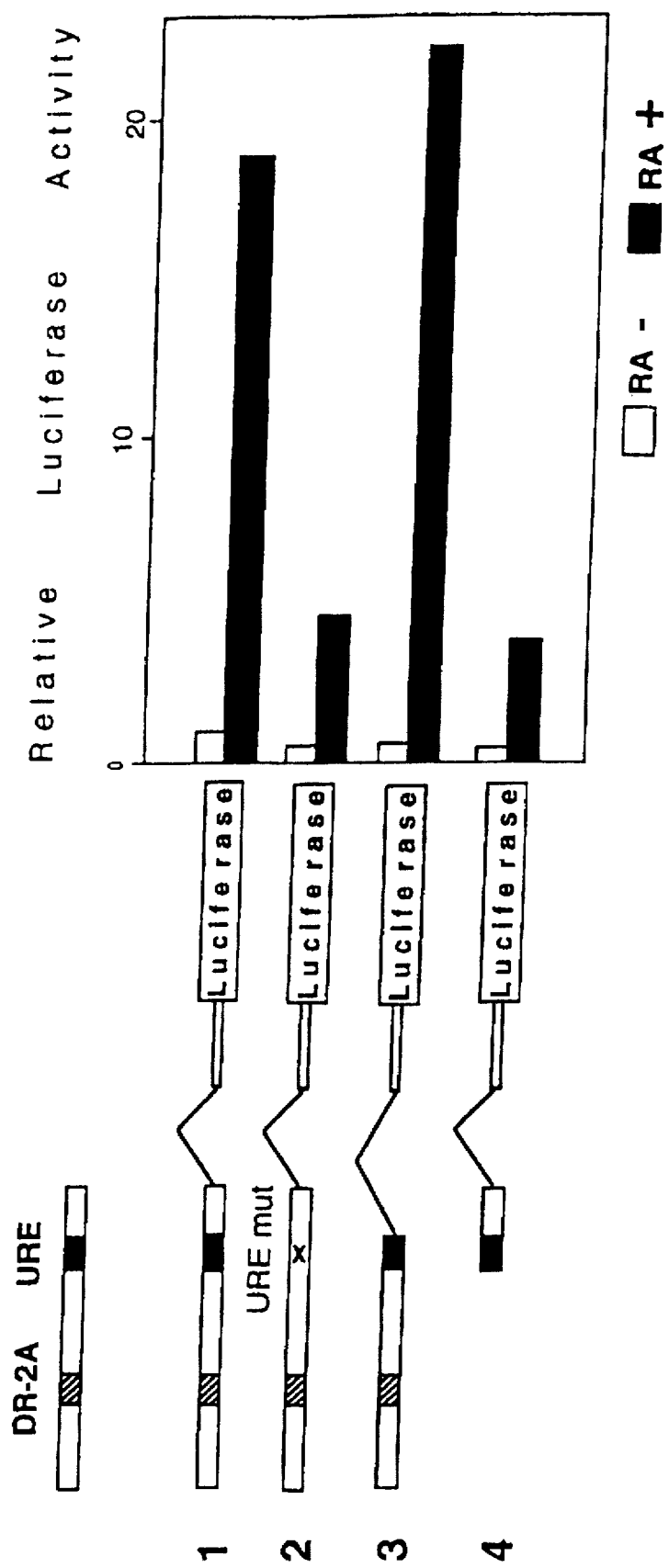
FIG. 1(D) presents activation profiles of deletion and URE mut constructs (constructs 1–4). The same basal HOXB1 promoter was used as described in FIGS. 1(A) and 1(B).

Interestingly, it has been found that the RIP-binding-site and the RARE, when tested independently as single copies, show relatively little transcription transactivation activity. Even two tandem copies of the RIP-binding-site show only a low-level basal activity and are essentially unresponsive to retinoic acid treatment (FIG. 1d). Similarly, two copies of the DR-2A site show only modest retinoic acid responsiveness when tested in the absence of the RIP-binding-site. However, when the RIP-binding-site and DR-2A are combined, full retinoid inducibility is synergistically regained. This demonstrates that high levels of retinoic acid activation require the co-stimulatory activity of the RIP-binding-site (URE), the RARE and their associated binding proteins.

Gel retardation analysis was used to identify and isolate the RIP-binding-site binding activity in nuclear extracts from P19 cells (i.e., RIP protein). In the absence of retinoic acid, only background levels of activity are observed for protein binding to the RIP-binding-site containing fragment. However, following retinoic acid treatment of P19 cells, nearly 100-fold induction of RIP binding activity is observed. RIP binding is specific for the RIP-binding-site (URE), as revealed by competition assays, and is not competed for by the RIP- binding-site mutant sequence shown in FIG.1c (SEQ ID NO:3). In contrast, no RIP-binding-site binding is observed in nuclear extracts from NT2/D1 cells (whether or not such cells have been treated with retinoic acid). These results demonstrate that in NT2/D1 cells, the isolated HOX reporter is totally inactive either before or after retinoic acid treatment (FIG. 1a, solid bars).

Interestingly, the NT2/D1 cells are retinoic acid responsive as indicated by the control TK reporter containing the ERE (discussed below; FIG. 2b lane 1). Furthermore, the NT2/D1 cells are known to undergo differentiation in response to retinoic acid (Andrews et al., 1984, Lab. Invest. 50:147–162). These results demonstrate that the deficiency of RIP precludes the promoter from responding to retinoic acid. This is consistent with the results shown in FIG. 1d indicating that the DR-2A site alone is incapable of producing a sustained retinoic acid response, and further support the view that retinoic acid responsiveness of the HOXB1 promoter is based on a cooperative interaction between the DR-2A, the RIP-binding-site (URE), and its associated binding protein (RIP). Thus, RIP functions as a type of retinoic acid-dependent cofactor.

These results identify a novel RIP-associated response element composed of a retinoic acid receptor response element (DR-2A) in association with a RIP-binding-site, which together confer retinoid responsiveness to the isolated HOXB1 promoter. Because of the dependence of the RIP-associated retinoic acid response on the presence of RIP protein, retinoic acid inducibility is observed in P19 cells (which endogenously express RIP) but not in NT2/D1 cells (which do not endogenously express RIP).

EXAMPLE 2

Isolation of a RA-Responsive Site Downstream of the HOXB1 Gene

It has been found that while the transfected HOXB1 promoter fails to respond to retinoic acid in NT2/D1 cells, the endogenous HOXB1 gene can still be activated in NT2/D1 cells (Simeone et al., 1990, Nature 346:763–767). The retention of inducibility of the intact gene indicated the potential existence of a second pathway for retinoic acid responsiveness that is not mediated by the promoter. The 3' portion of the HOXB1 gene between the promoter and a repetitive DNA cluster was searched for such an alternate pathway. Analysis of the 3' portion indicated that virtually the entire HOX B cluster, which is more than 100 kb long, is essentially free of repetitive DNA. This unique sequence of DNA contains a 7 kb region downstream of the 3' end of the HOXB1 gene, after which numerous repetitive sequence elements are found.

Figure 2A:
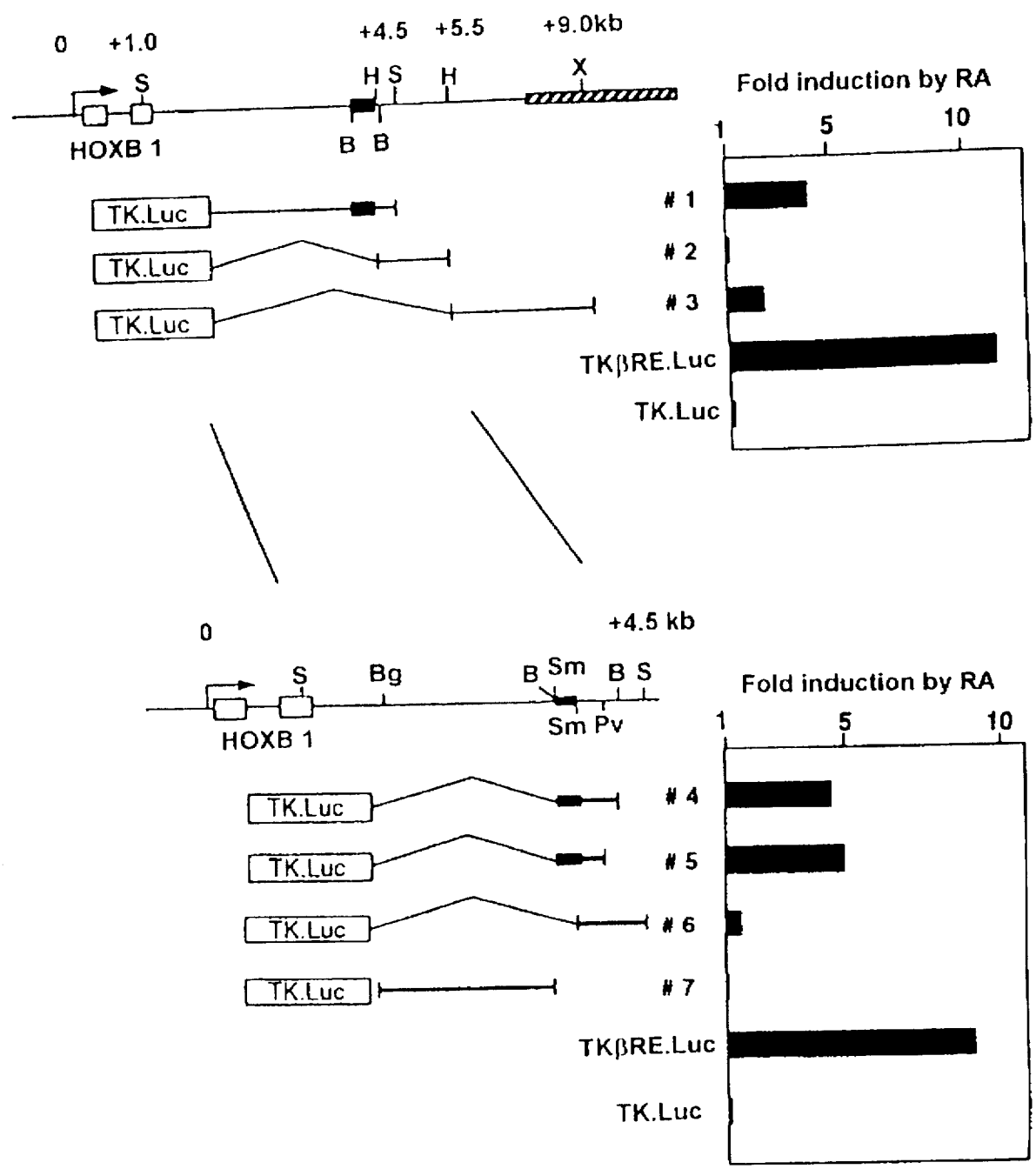
FIG. 2(A) shows the localization of a retinoic acid-responsive site downstream of the HOXB1 gene. Six different TK.Luciferase plasmids shown in the figure were made by inserting various DNA fragments derived from HOXB1 3' region into the 3' side of TK.Luciferase gene, and transfected into P19 cells. The filled box in the map indicates a putative RARE. Restriction site designations are as follows: B:BamHI, H:HindIII, S:SacI, X:XbaI.
Figure 2B:
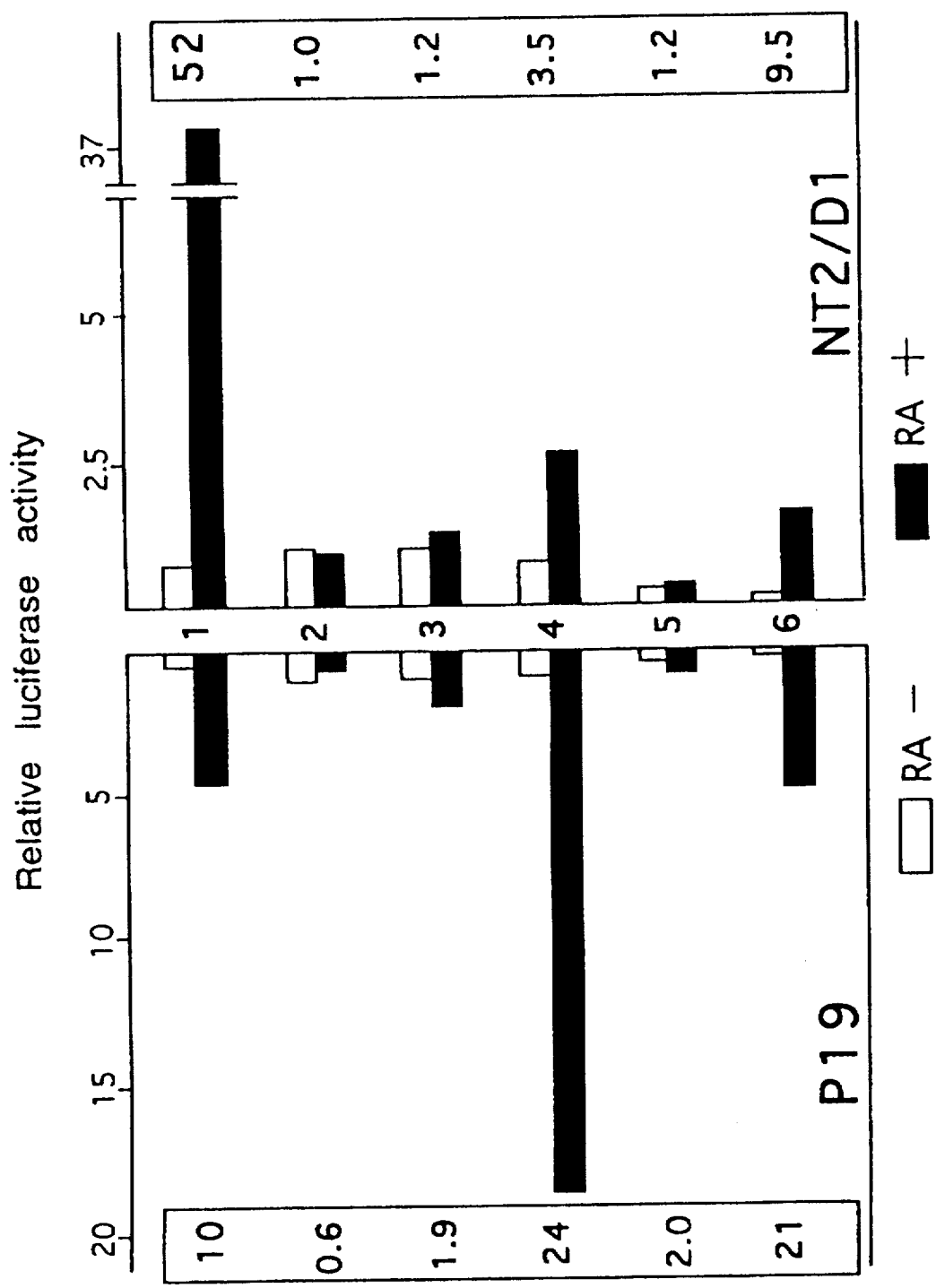
FIG. 2(B) presents results which indicate that the DR-2B motif activates TK and HOXB1 (HXB) promoters from a downstream position. Activation profiles derived from six different plasmids are shown. All plasmids were transfected into P19 and NT2/D1 cells. The numbers in boxes at the left- and right-hand margins of the figure indicate fold induction by 1 µM of retinoic acid in P19 and NT2/D1 cells, respectively. The constructs used were as follows: construct 1=TKβRE.Luc, construct 2=TK.Luc, construct 3=TK.Luc (DR2B)$_1$, construct 4=TK.Luc (DR2B)$_3$, construct 5=HXB.Luc, and construct 6=HXB.Luc (DR2B)$_3$.

Constructs containing a variety of fragments from this 7 kb 3' downstream region were produced, and are shown in FIG. 2a. After addition of a SalI linker, the TK.Luciferase gene was inserted into the SalI site of pBluescript SK+vector (Stratagene) to produce the plasmid pBS-TK.Luc. The human HOXB1 3' region was subcloned into pBS-TK.Luc. The genomic DNA fragments derived from the 3' region of HOXB1 were ligated into a TK.luc reporter in a fashion that preserves the natural downstream genomic configuration. The promoter of the herpes simplex virus thymidine kinase gene (TK promoter) was used in the constructs to establish the independence of this regulation from the HOX promoter. As shown in FIG. 2a, construct #1 containing the SacI fragment of +1.0 to +4.5 kb retained the same basal luciferase activity as parental Tk.luc, but was activated 4-fold in response to 1 μM of retinoic acid. The adjacent HindIII fragment of +4.0 to +5.5 kb (#2) did not confer responsiveness to retinoic acid, while construct #3 (approximately +5.5 to +9.5 kb) displayed weak responsiveness. Plasmid tkβRE.luc which has a DR-5 type RARE from RARβ2 promoter (Sucov et al., 1990, PNAS, USA 87:5392–5396) was induced 11-fold. Parental plasmid Tk.luc was not affected by retinoic acid. It can thus be concluded that the +1.0 to +4.5 kb SacI fragment contains a retinoic acid response element.

To localize this putative regulatory sequence, the SacI fragment (+1.0 to +4.5) was subdivided into a series of nested constructs. Results using these constructs indicate that retinoic acid activates constructs #4 and #5, which share 0.2 kb BamHI-SmaI region (shown in FIG. 2A as a thick line) while marginal or no inducibility was observed for the fragments in constructs #6 and #7 (FIG. 2a). These results indicated that attention should be focussed on the 0.2 kb BamHI-SmaI fragment for the identification and isolation of the downstream response element.

Deletion analysis of the 0.2 kb BamHI-SmaI fragment was used to localize retinoic acid responsiveness to a 5' 110 nucleotide subfragment. The sequence of this region includes a direct repeat of 5'-AGGT(A/C)A-3' (in antisense orientation) spaced by 2 nucleotides (referred to herein as DR-2B; nucleotides 41–54 of SEQ ID NO:2). No other other RARE motif was found from sequence analysis of 1.6 kb spanning this region. To further analyze retinoic acid responsiveness, an oligonucleotide containing this DR-2B sequence (corresponding to nucleotides 35–59 of SEQ ID NO:2) was ligated into the 3' end of the Tk.luc transcription unit as single and triple copies (TK.luc(DR2B)$_1$ or TK.luc (DR2B)$_3$, respectively). These constructs were transfected into P19 and NT2/D1 cells and examined for hormonal response. Following addition of 1 μM of retinoic acid, the construct harboring three DR-2B motifs (FIG. 2b, lane 4) displayed robust inducibility (24-fold) in P19 cells, yet only a weak response in NT2/D1 cells. A single DR-2B showed only weak transcriptional activation activity in either cell (FIG. 2b, lane 3). The TKβRE.luc control plasmid induced luciferase reporter protein expression 10 and 50 fold in P19 and NT2/D1 cells, respectively (lane 1), while the parental TK.luc control vector (lane 2) did not respond to retinoic acid.

To test whether the DR-2B response element motif confers retinoic acid-inducibility to the HOXB1 promoter, plasmids HXB.Luc and HXB(DR-2B)$_3$, which substitutes the SpeI-NcoI promoter fragment (shown in FIG. 1a) of HOXB1 (not including the URE) for the TK promoter in the plasmids TK.luc and TK.luc(DR2B), were constructed. Transfection and luciferase assays were conducted as described in Example 1. A control TKβRE.Luc was used that has one copy of DR-5 type motif found in the promoter of RARβ gene at 5' side of TK promoter.

While the promoter alone is only marginally active (FIG. 2b, lane 5), the HXB(DR-2B)$_3$ plasmid containing the DR-2B response element confers efficient (21-fold) induction of transcription in P19 cells (FIG. 2b, lane 6). Similar inducibility was observed in F9 cells (ATCC #CRL 1720), while NT2/D1 cells show a positive but less effective response. However, as shown below, NT2/D1 cells contain low levels of RAR and RXR receptors, and response in these cells is markedly potentiated by co-transfection of RAR and RXR expression vectors. Together these results demonstrate that the HOXB1 DR-2B response element can function as an RARE in two embryonal carcinoma cell lines.

EXAMPLE 3

Demonstration of RAR:RXR Heterodimer Formation on DR-2A and DR-2B Motifs

The ability of RAR and RXR to form either homo- or heterodimers on the HOXB1 DR-2A and DR-2B response elements was examined using gel retardation assays. The expression plasmids pCMX-hRARα and pCMX-hRXRα were linearized with NheI restriction enzyme. Subsequently, capped mRNA was synthesized in vitro using T7 RNA polymerase (Stratagene) according to the manufacturer's instructions. Aliquots of mRNA were incubated with rabbit reticulocyte lysate (Promega) for in vitro translation. Human RARα and RXRα proteins were synthesized by in vitro translation and mixed with $P^{32}$ labelled response elements from the RARβ2 RARE (a DR-5 response element) and the HOXB1 DR-2A and DR-2B response elements followed by gel electrophoresis. 5 μl of in vitro translated proteins were used for gel retardation assays according to the methods described in Kliewer et al., (1992) Nature 355:446—449.

Results from the gel-retardation assay confirm that high affinity binding of RAR and RXR heterodimers to the DR-5 motif as reported previously. Similar RAR:RXR heterodimer binding was observed on the HOXB1 DR-2A probe and HOXB1 DR-2B probe. Although the specific activity of the probes was the same, RAR:RXR heterodimer binding to the DR-2 response elements was less intense than the heterodimer binding on the DR-5 response element. This is in agreement with previous results that suggest that RAR-RXR heterodimers may form lower affinity complexes on the DR-2 motif. The heterodimeric nature of these receptor complexes was confirmed using a supershift assay in which rabbit polyclonal antibodies against RARα and RXRα were incubated with a receptor-DNA mixture.

Figure 3:
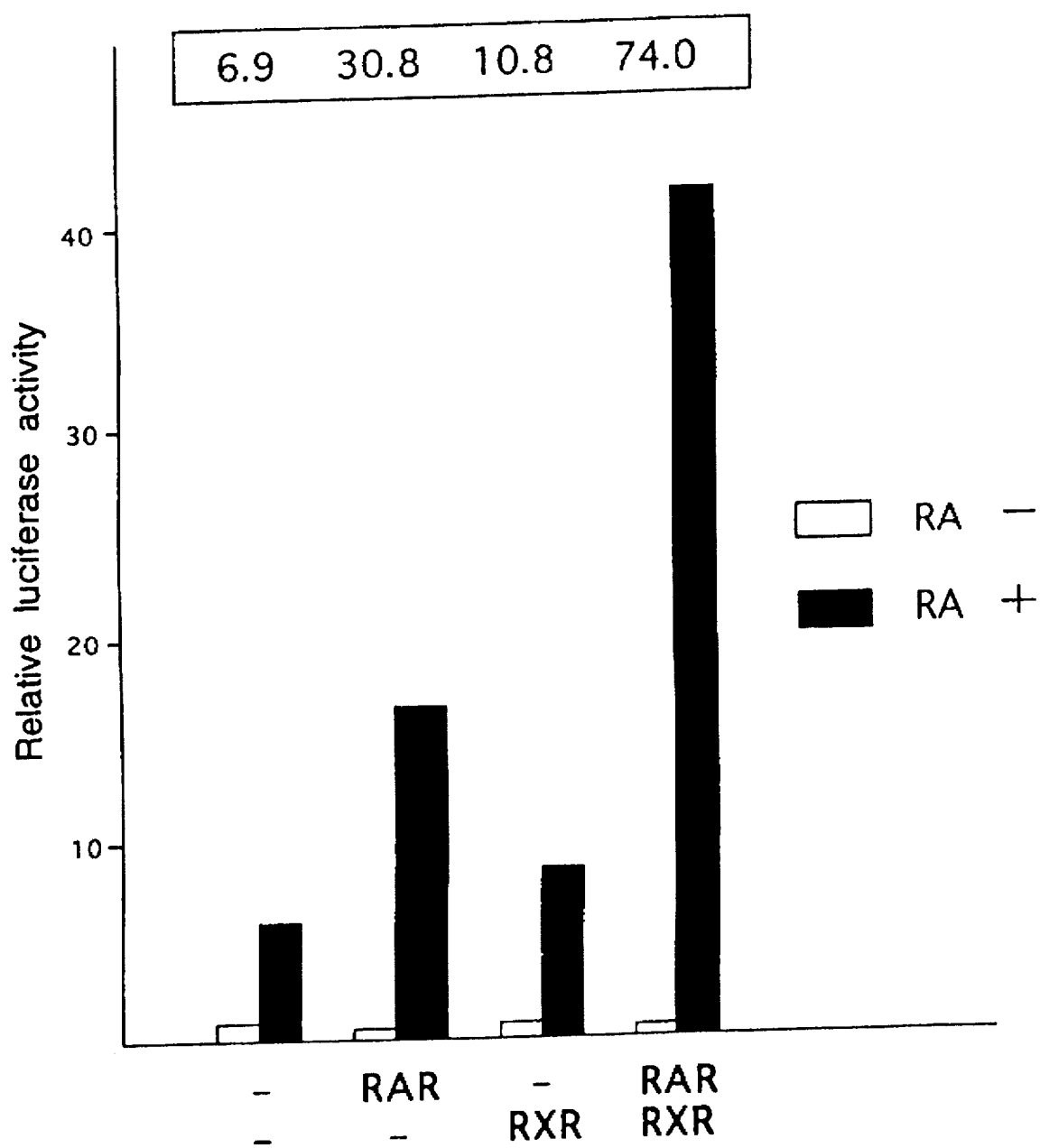
FIG. 3 presents results from an assay for the action of RARα and RXRα on DR-2 motif. TK.Luc (DR2B)$_2$ (2 copies of DR-2B) was transfected into NT2/D1 cells with CMX-hRARα and/or CMX-hRXRα. The numbers in box across the top of the figure indicate fold induction by retinoic acid.

To explore the intracellular roles of the RAR:RXR receptor heterodimer on HOX gene regulation via the DR-2B RARE, the Tk.luc $(DR-2B)_2$ reporter plasmid was transfected with RARα and/or RXRα expression vectors into NT2/D1 cells. Transfections and luciferase assays were conducted as described above, except 0.1 μg of CMX-hRARα and/or CMX-hRXRα were co-transfected. As shown in FIG. 3, dramatic synergism was observed when both RARα and RXRα were co-transfected. When TK.luc $(DR-2B)_2$ was transfected alone, without co-transfection of the RARα and RXRα expression vectors, expression of the luciferase reporter proteins was induced only 7-fold by retinoic acid. When either the RARα or RXRα were each individually co-transfected with TK.luc$(DR-2B)_2$, transactivation of luciferase reporter protein expression was enhanced 31-fold and 11-fold, respectively. When both RARα and RXRα were co-transfected with TK.luc(DR-2B)$_2$, a remarkable synergistic effect on transactivation of luciferase expression was observed (74-fold induction). From these DNA binding and transactivation assays, it can be concluded that the DR-2B serves as an effective target for the RAR:RXR heterodimer.

EXAMPLE 4

Figure 4:
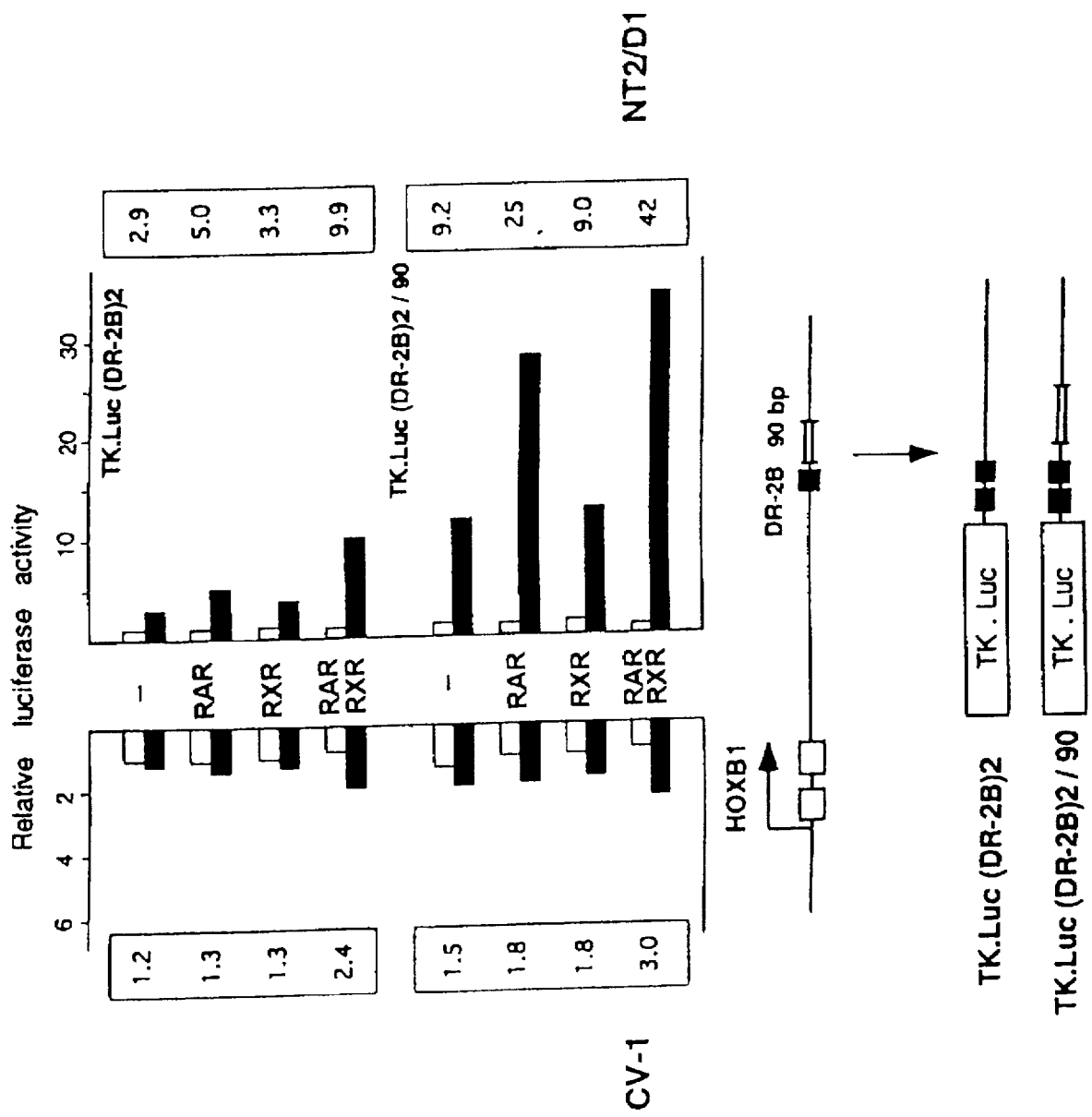
FIG. 4 provides results from an assay identifying a downstream retinoic acid co-activator. The numbers in boxes at the left and right margins of the figure indicate fold induction by retinoic acid in CV-1 and NT2/D1 cells, respectively.
Figure 5:
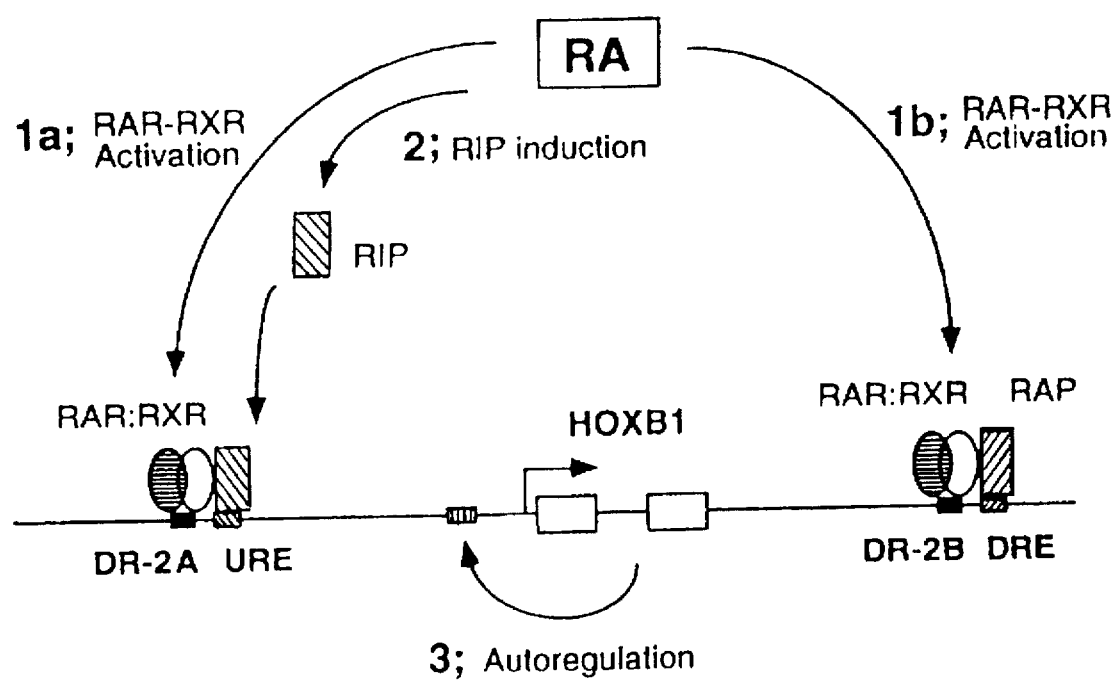
FIG. 5 shows a three step cascade for retinoic acid activation of the HOXB1 promoter. This diagram illustrates multiple and overlapping activation pathways. retinoic acid activates the HOXB1 promoter through both upstream and downstream response elements. Both response elements comprise two functionally separable components. The first components are the DR-2A and DR-2B sequences (RAREs) which are direct targets for the RAR-RXR heterodimer (designated as pathway 1a and respectively). The second components of each response element bind to cell specific co-activators. The DR-2A co-activator protein (RIP:Retinoid Induced Protein) is strongly induced in P19 cells by retinoic acid and binds to an upstream response element motif (RIP-binding-site) near DR-2A (designated as pathway 2). The third pathway is auto-regulation (designated as pathway 3), wherein activation of HOXB1 gene by retinoic acid leads to active auto-regulatory loop that potentiates the retinoic acid effect.

Assay the Effect of the HOXB1 DR-2B Response Element in Combination With a RAP-Binding-Site As observed in Example 2 (FIGS. 2a and 2b), a restriction fragment including sequences flanking the DR-2B response element motif served as a better response element than the synthetic DR-2B motif alone. To test whether an additional site in constructs #4 and #5 (FIG. 2a) might act cooperatively to enhance the function of the DR-2 response element motif, three new constructs were generated and designated TK.Luc$(DR-2B)_2$, TK.Luc$(DR-2B)_2$/90, and TK/90 (FIG. 4). To generate these constructs, two copies of DR-2B oligonucleotide were introduced into the 3' side of TK.Luciferase transcription unit to create the plasmid TK.Luc $(DR2B)_2$. A 90 bp fragment (shown as a double line in FIG. 4) containing the RAP-binding-site was generated by PCR and inserted downstream from the DR-2B sequence (shown as blocks) to produce the plasmid TK.Luc$(DR-2B)_2$/90. A control plasmid TK.Luc/90 was produced by placing only the 90 base pair RAP-binding-site fragment at the downstream 3' side of TK.Luciferase.

These plasmids were transfected into NT2/D1 cells and monitored for retinoic acid responsiveness in the presence of co-transfected RAR and RXR expression plasmids. Transfections and luciferase assays were conducted as described in Example 1. As shown in FIG. 3, synergistic transactivation was observed on the reporter plasmid TK.Luc$(DR-2B)_2$ by RAR and RXR. Unexpectedly, more profound transactivation was observed on the reporter plasmid. TK.Luc(DR-2B)$_2$/90. No transactivation in response to retinoic acid was observed in NT2/D1 cells transfected with the TK.Luc/90 plasmid (only 90 bp fragment was inserted). These results demonstrate the enhancement of transactivation on the DR-2B response element by the 90 bp fragment containing the invention RAP-binding-site. A similar enhancing effect was observed in P19 cells.

These results demonstrate that the HOXB1 RARE activity is augmented by an adjacent RAP-binding-site potentiating sequence. Interestingly, the 90 bp fragment containing the RAP-binding-site sequence failed to augment retinoic acid responsiveness in CV-1 cells with RAR and/or RXR expression vectors (FIG. 4). A gel retardation assay was conducted using the 90 bp region (i.e., RAP-binding-site) as a probe, and a protein referred to as RAP (Retinoid Activating Protein) was identified and isolated in NT2/D1 cell nuclear extracts (but not in CV-1 cell extracts) which specifically binds to this region. This supports the previous transfection data and demonstrates that, in a fashion similar to the 5' RARE (DR-2A), the unique combination of DR-2B and RAP-binding-site regulatory sequences gives rise to a cell-type specific retinoic acid response element (referred to herein as RAP-associated response element).

While the invention has been described in detail with reference to certain preferred embodiments thereof, it will be understood that modifications and variations are within the spirit and scope of that which is described and claimed.

---

That which is claimed is:

1. A bioassay for evaluating whether a compound is a functional ligand for a functional retinoid receptor protein, said bioassay comprising:
   (a) culturing cells which contain:
      functional retinoid receptor protein,
      a protein selected from a retinoid-inducible protein (RIP) or a retinoid-activating protein (RAP), and
      DNA comprising an enhanced-response-element operatively linked to an heterologous reporter gene;
      wherein said culturing is conducted in the presence of at least one compound whose ability to function as a ligand for said functional retinoid receptor protein is sought to be determined; and
   (b) assaying for evidence of transcription of said reporter gene in said cells;
   wherein said enhanced-response-element is a RIP-associated response element or a RAP-associated response element,
   wherein a RIP-associated response element is employed in cells which contain a RIP protein and a RAP-associated response element is employed in cells which contain a RAP protein,
   wherein said RIP-associated response element comprises:
      a RIP-binding-site, and
      a direct repeat sequence to which said retinoid receptor binds;
   wherein said RIP-binding-site has the nucleotide sequence of nucleotides 91–102 of SEQ ID NO:1,
   wherein modifications can be made: to any single triplet selected from nucleotides 91–93, 97–99 or 100–102 of SEQ ID NO:1, or
   to the triplet sequences of both nucleotides 91–93 and 97–99, provided that the resulting sequence remains a palindrome and retains RIP-binding activity;
   wherein said RAP associated response element comprises:
      a RAP-binding-site, and
      a direct repeat sequence to which said retinoid receptor binds;
   wherein said RAP-binding-site has the nucleotide sequence of nucleotides 101–116 of SEQ ID NO:2, or sequences of the same length which are at least 70% identical thereto, provided such sequences retain RAP-binding activity.

2. A bioassay according to claim 1, wherein said retinoid receptor protein is expressed from heterologous DNA.

3. A bioassay according to claim 1, wherein said retinoid receptor is a RXR-RAR heterodimer complex.

4. A bioassay according to claim 1, wherein the cells are vertebrate.

5. A bioassay according to claim 4, wherein the cells are mammalian.

6. A bioassay according to claim 5, wherein said cells are selected from P19 cells or NT2/D1 cells.

7. A bioassay according to claim 1, wherein said direct repeat sequence has the following structure:

5'-RGBNNM-[(NN)-RGBNNM]$_y$-3' (SEQ ID NO:7),
   wherein
   each R is independently selected from A or G;
   each B is independently selected from G, C, or T;
   each N is independently selected from A, T, C, or G; and
   each M is independently selected from A or C; with the proviso that at least 4 nucleotides of each -RGBNNM- group of nucleotides are identical with the nucleotides at comparable positions of the sequence -AGGTCA-, and
   y is at least 1.

8. A bioassay according to claim 7, wherein each -RGBNNM- group is independently selected from -AGGGCA-, -AGTTCA-, -AGGTAA-, -AGGTCA-, -GGTTCA-, -GGGTTA-, -GGGTGA-, -AGGTGA-, or -GGGTCA-.

9. A bioassay according to claim 7, wherein said first -RGBNNM- group is -AGGGCA-.

10. A bioassay according to claim 7, wherein said second -RGBNNM- group is -AGTTCA-.

11. A bioassay according to claim 7, wherein said nucleotide sequence
   -AGGGCA-TC-AGTTCA- (SEQ ID NO:4).

12. A bioassay according to claim 7, wherein said first -RGBNNM- group is -AGGTAA-.

13. A bioassay according to claim 7, wherein said second -RGBNNM- group is -AGGTCA-.

14. A bioassay according to claim 7, wherein said nucleotide sequence is:

-AGGTAA-TT-AGGTCA- (SEQ ID NO:5).

15. A bioassay for detecting a compound that is an antagonist for a functional retinoid receptor, said bioassay comprising:

(a) culturing test cells in a series of culture media containing:
  increasing concentrations of at least one compound whose ability to inhibit the transcription activation activity of retinoid receptor agonists is sought to be determined, and
  a fixed concentration of at least one agonist for said functional retinoid receptor; and thereafter (b) assaying the amount of transcription of said reporter gene in said cells as a function of the concentration of said compound in said culture media, thereby indicating the ability of said compound to inhibit activation of transcription by retinoid receptor agonists;

wherein said test cells contain:
  functional retinoid receptor,
  a protein selected from a retinoid-inducible protein (RIP) or a retinoid-activating protein (RAP),
  DNA comprising an enhanced-response-element operatively linked to an heterologous reporter gene, wherein said enhanced-response-element is a RIP-associated response element or a RAP-associated response element;
  wherein a RIP-associated response element is employed in cells which contain a RIP protein and a RAP-associated response element is employed in cells which contain a RAP protein,
  wherein said RIP-associated response element comprises:
    a RIP-binding-site, and
    a direct repeat sequence to which said retinoid receptor binds;
    wherein said RIP-binding-site has the nucleotide sequence of nucleotides 91–102 of SEQ ID NO:1,
    wherein modifications can be made: to any single triplet selected from nucleotides 91–93, 97–99 or 100–102 of SEQ ID NO:1, or
    to the triplet sequences of both nucleotides 91–93 and 97–99, provided that the resulting sequence remains a palindrome and retains RIP-binding activity;
  wherein said RAP associated response element comprises:
    a RAP-binding-site, and
    a direct repeat sequence to which said retinoid receptor binds;
    wherein said RAP-binding-site has the nucleotide sequence of nucleotides 101–116 of SEQ ID NO:2, or sequences of the same length which are at least 70% identical thereto, provided such sequences retain RAP-binding activity.

16. A bioassay according to claim 15, wherein said retinoid receptor is expressed from heterologous DNA.

17. A bioassay according to claim 15, wherein said retinoid receptor is a RXR-RAR heterodimer complex.

18. A bioassay according to claim 15, wherein said direct repeat sequence has the following structure:

5'-RGBNNM-[(NN)-RGBNNM]$_y$-3' (SEQ ID NO:7), wherein
  each R is independently selected from A or G;
  each B is independently selected from G, C, or T;
  each N is independently selected from A, T, C, or G; and
  each M is independently selected from A or C; with the proviso that at least 4 nucleotides of each -RGBNNM- group of nucleotides are identical with the nucleotides at comparable positions of the sequence -AGGTCA-, and
  y is at least 1.

19. A method for testing the activity of a test compound as an agonist for a retinoid receptor, said method comprising:

(a) culturing cells transformed with:
  a recombinant expression vector in the presence of an intracellular retinoid receptor,
  an intracellular protein selected from a retinoid-inducible protein (RIP) or a retinoid-activating protein (RAP), and in the further presence, or in the absence, of the test compound,
  wherein said vector further comprises a DNA construct having:
    an enhanced-response-element operatively associated with a promoter, so as to confer transcriptional activation activity on said promoter in the presence of a functional ligand, its associated retinoid receptor, and a RIP or a RAP,
    a gene which encodes a reporter protein, wherein said gene is operatively linked to said promoter; and thereafter (b) selecting test compounds that increase the amount of reporter protein expression relative to expression levels in the absence of said test compound;
  wherein said enhanced-response-element is a RIP-associated response element or a RAP-associated response element,
  wherein a RIP-associated response element is employed in cells which contain a RIP protein and a RAP-associated response element is employed in cells which contain a RAP protein, and
  wherein said RIP-associated response element comprises:
    a RIP-binding-site, and
    a direct repeat sequence to which said retinoid receptor binds;
    wherein said RIP-binding-site has the nucleotide sequence of nucleotides 91–102 of SEQ ID NO:1,
    wherein modifications can be made: to any single triplet selected from nucleotides 91–93, 97–99 or 100–102 of SEQ ID NO:1, or
    to the triplet sequences of both nucleotides 91–93 and 97–99 provided that the resulting sequence remains a palindrome and retains RIP-binding activity;
  wherein said RAP associated response element comprises:
    a RAP-binding-site, and
    a direct repeat sequence to which said retinoid receptor binds;
    wherein said RAP-binding-site has the nucleotide sequence of nucleotides 101–116 of SEQ ID NO:2, or sequences of the same length which are at least 70% identical thereto, provided such sequences retain RAP-binding activity.

20. A bioassay according to claim 19, wherein said retinoid receptor is a RXR-RAR heterodimer complex.

21. A bioassay according to claim 19, wherein said direct repeat sequence has the following structure:

5'-RGBNNM-[(NN)-RGBNNM]$_y$-3' (SEQ ID NO: 7), wherein
each R is independently selected from A or G;
each B is independently selected from G, C, or T;
each N is independently selected from A, T, C, or G; and
each M is independently selected from A or C; with the proviso that at least 4 nucleotides of each -RGBNNM- group of nucleotides are identical with the nucleotides at comparable positions of the sequence -AGGTCA-, and
y is at least 1.

22. A method for testing the activity of a test compound as an antagonist of ligand for a retinoid receptor, said method comprising:

(a) culturing cells transformed with a recombinant expression vector in the presence of an intracellular retinoid receptor, a protein selected from a retinoid-inducible protein (RIP) or a retinoid-activating protein (RAP), said ligand, and further:
  (i) in the presence of the test compound, or
  (ii) in the absence of the test compound;
wherein said vector further comprises a DNA construct having:
  an enhanced-response-element operatively associated with a promoter, so as to confer transcriptional activation activity on said promoter in the presence of a functional ligand, its associated retinoid receptor, and a RIP or a RAP, and
  a gene which encodes a reporter protein, wherein said gene is operatively linked to said promoter; and thereafter (b) selecting test compounds that decrease the amount of reporter protein expression relative to expression levels in the absence of said test compound;
  wherein said enhanced-response-element is a RIP-associated response element or a RAP-associated response element,
  wherein a RIP-associated response element is employed in cells which contain a RIP protein and a RAP-associated response element is employed in cells which contain a RAP protein,
  wherein said RIP-associated response element comprises:
    a RIP-binding-site, and
    a direct repeat sequence to which said retinoid receptor binds;
  wherein said RIP-binding-site has the nucleotide sequence of nucleotides 91-102 of SEQ ID NO:1,
  wherein modifications can be made: to any single triplet selected from nucleotides 91-93, 97-99 or 100-102 of SEQ ID NO:1, or
  to the triplet sequences of both nucleotides 91-93 and 97-99, provided that the resulting sequence remains a palindrome and retains RIP-binding activity;
  wherein said RAP associated response element comprises;
    a RAP-binding-site, and
    a direct repeat sequence to which said retinoid receptor binds;
  wherein said RAP-binding-site has the nucleotide sequence of nucleotides 101-116 of SEQ ID NO:2, or sequences of the same length which are at least 70% identical thereto, provided such sequences retain RAP-binding activity.

23. A method according to claim 22, wherein said ligand is retinoic acid or a derivative thereof.

24. A method according to claim 22, wherein said direct repeat sequence has the following structure:

-RGBNNM-[(NN)-RGBNNM]$_y$-3' (SEQ ID NO:7), wherein
each R is independently selected from A or G;
each B is independently selected from G, C, or T;
each N is independently selected from A, T, C, or G; and
each M is independently selected from A or C; with the proviso that at least 4 nucleotides of each -RGBNNM- group of nucleotides are identical with the nucleotides at comparable positions of the sequence -AGGTCA-, and
y is at least 1.

* * * * *